US008802828B2

(12) United States Patent
Seefeldt et al.

(10) Patent No.: US 8,802,828 B2
(45) Date of Patent: Aug. 12, 2014

(54) HIGH PRESSURE REFOLDING OF MONOCLONAL ANTIBODY AGGREGATES

(75) Inventors: Matthew B. Seefeldt, Denver, CO (US); Robert Nelson, Arvada, CO (US); Theodore W. Randolph, Niwot, CO (US); Lyndal K. Hesterberg, Boulder, CO (US)

(73) Assignee: Barofold, Inc., Aurora, CO (US)

( * ) Notice: Subject to any disclaimer, the term of this patent is extended or adjusted under 35 U.S.C. 154(b) by 0 days.

(21) Appl. No.: 13/405,573

(22) Filed: Feb. 27, 2012

(65) Prior Publication Data

US 2012/0245329 A1    Sep. 27, 2012

Related U.S. Application Data (63) Continuation of application No. 12/208,193, filed on Sep. 10, 2008, now abandoned.

(60) Provisional application No. 60/971,223, filed on Sep. 10, 2007.

(51) Int. Cl.
    *C07K 17/00* (2006.01)
(52) U.S. Cl.
    USPC .......................................... 530/412; 530/413
(58) Field of Classification Search
    None
    See application file for complete search history.

(56) References Cited

U.S. PATENT DOCUMENTS

| | | | |
|---|---|---|---|
| 6,489,450 B2 * | 12/2002 | Randolph et al. ............. 530/427 |
| 7,064,192 B2 | 6/2006 | Randolph |
| 7,538,198 B2 | 5/2009 | Randolph |
| 7,767,795 B2 | 8/2010 | Randolph |
| 7,829,681 B2 | 11/2010 | Seefeldt |
| 2008/0161242 A1 | 7/2008 | Randolph |
| 2008/0249286 A1 | 10/2008 | Seefeldt |
| 2009/0215998 A1 | 8/2009 | Antman |
| 2010/0075399 A1 | 3/2010 | Randolph |
| 2010/0255536 A1 | 10/2010 | Randolph |
| 2011/0046357 A1 | 2/2011 | Randolph |
| 2011/0070219 A1 | 3/2011 | Seefeldt |

FOREIGN PATENT DOCUMENTS

| WO | WO 02/062827 | 8/2002 |
|---|---|---|
| WO | WO 2008/033555 | 3/2008 |

OTHER PUBLICATIONS

Genovese et al, NEJM, vol. 353, No. 1114-1123, 2005.*
International Preliminary Report on Patentability and Written Opinion of the International Searching Authority issued in connection with PCT/US2008/010595 on Mar. 16, 2010.
International Search Report issued in connection with PCT/US2008/010595 on Dec. 30, 2008.
Thommes, et al. (2007) "Alternatives to Chromatographic Separations" Biotechnol. Progress, 23(1):42-45.
Gabrielson, et al. (2007) "Quantitation of Aggregate Levels in a Recombinant Humanized Monoclonal Antibody Formulation by Size-Exclusion Chromatography, Asymmetrical Flow Field Fractionation and Sedimentation Velocity," J. Pharmaceutical Sci., 96(2):268-279.
Pree, et al. (2006) "New Approaches to Prevent Transplant Rejection: Co-Stimulation Blockers Anti-CD40L and CTLA-4Ig," Drug Discovery Today, 3(1):41-47.
Seefeldt, et al. (2004) "High-Pressure Refolding of Bikunin: Efficacy and Thermodynamics," Protein Science, 13(10):2639-2650.
Qoronfleh, et al. (2007) "Confronting High-Throughput Protein Refolding Using High Pressure and Solution Screens," Protein Expression and Purification, 55(2):209-224.
Phelps, et al. (2007) "Protein Disaggregation and Refolding Using High Hydrostatic Pressure," J. Chem. Technol., 82(7):610-613.
St. John et al, (2001) "High Pressure Refolding of Recombinant Human Growth Hormone from Insoluble Aggregates. Structural Transformations, Kinetic Barriers, and Energentics," J. Biol. Chem., 276(50):46856-46863.

* cited by examiner

*Primary Examiner* — Yunsoo Kim
(74) *Attorney, Agent, or Firm* — Cooley LLP (57) ABSTRACT

Methods for refolding antibodies, particularly monoclonal antibodies, from aggregated and/or denatured preparations by subjecting the antibody preparation to high hydrostatic pressure are provided. Refolded preparations of antibodies produced by the methods described herein are also provided.

5 Claims, 6 Drawing Sheets

HIGH PRESSURE REFOLDING OF MONOCLONAL ANTIBODY AGGREGATES

CROSS REFERENCE TO RELATED APPLICATIONS

This application is a continuation of application Ser. No. 12/208,193, filed Sep. 10, 2008, which claims the priority benefit of U.S. Provisional Patent Application No. 60/971,223, filed on Sep. 10, 2007. The entire contents of that those applications are hereby incorporated by reference herein.

FIELD OF THE INVENTION

This invention relates to the high pressure refolding of antibody aggregates, and in particular monoclonal antibody aggregates.

BACKGROUND OF THE INVENTION

Many proteins are valuable as therapeutic agents. Protein therapeutics are often produced using recombinant DNA technology, which can enable production of higher amounts of protein than can be isolated from naturally-occurring sources, and which avoids contamination that often occurs with proteins isolated from naturally-occurring sources.

Proper folding of a protein is essential to the normal functioning of the protein. Improperly folded proteins are believed to contribute to the pathology of several diseases, including Alzheimer's disease, bovine spongiform encephalopathy (BSE, or "mad cow" disease) and human Creutzfeldt-Jakob disease (CJD), and Parkinson's disease; these diseases serve to illustrate the importance of proper protein folding.

Proteins of therapeutic value in humans can be expressed in bacteria, yeast, and other microorganisms. While large amounts of proteins can be produced in such systems, the proteins are often misfolded, and often aggregate together in large clumps called inclusion bodies. The proteins cannot be used in the misfolded, aggregated state. Accordingly, methods of disaggregating and properly refolding such proteins have been the subject of much investigation.

One method of refolding proteins uses high pressure on solutions of proteins in order to disaggregate, unfold, and properly refold proteins. Such methods are described in U.S. Pat. No. 6,489,450, U.S. Pat. No. 7,064,192, U.S. Patent Application Publication No. 2004/0038333, and International Patent Application WO 02/062827. Those disclosures indicated that certain high-pressure treatments of aggregated proteins or misfolded proteins resulted in recovery of disaggregated protein retaining biological activity (i.e., the protein was properly folded, as is required for biological activity) in good yields. U.S. Pat. No. 6,489,450, U.S. Pat. No. 7,064,192, U.S. 2004/0038333, and WO 02/062827 are incorporated by reference herein in their entireties.

Certain devices have also been developed which are particularly suitable for refolding of proteins under high pressure; see International Patent Application Publication No. WO 2007/062174, which is incorporated by reference herein in its entirety.

Several monoclonal antibodies are currently in use as therapeutic agents, for example, Herceptin® (Trastuzumab) (Herceptin® is a registered trademark of Genentech, Inc., South San Francisco, Calif., for a monoclonal antibody useful in treating breast cancer) and Remicade® (Infliximab) (Remicade® is a registered trademark of Centocor, Inc., Malvern, Pa., for a monoclonal antibody useful in treating inflammatory disorders involving the immune system such as rheumatoid arthritis). Unfortunately, some of the most widely used processing steps for monoclonal antibody production, such as Protein A/G affinity purification and/or viral inactivation steps, require use of solutions at pH levels as low as approximately pH 3.0 during typical pharmaceutical protein manufacturing (Ejima et al., Proteins, 66:954-62 (2007)). Monoclonal antibodies readily aggregate during treatment at pH 3.0, possibly due to destabilization of the Fc domain. These aggregates can be difficult to remove and result in increased production costs. See, Thommes, J. and M. Etzel, Biotechnology Progress 23(1): 42-45 (2007) for a discussion of these issues. High pressure refolding provides a viable method for alleviating aggregation of monoclonal antibodies induced by manufacturing processes.

The effect of aggregate formation conditions on the pressure-modulated refolding yield is currently unknown. An earlier report (St. John, R. J., J. F. Carpenter, et al., Journal of Biological Chemistry 276(50): 46856-46863 (2001)) showed that the refolding yields of recombinant human growth hormone from two different insoluble aggregates contained different secondary structures and resulted in different refolding kinetics and yields. Thus, protein aggregates produced by different stresses exhibited different refolding behaviors. Consequently, the specific conditions required for refolding mAb aggregates formed after incubation at pH 3.0 may be unpredictable.

The instant invention provides methods useful in refolding monoclonal antibody aggregates produced after exposure to low pH, for example, approximately pH 3.0, as well as preparations containing such monoclonal antibody aggregates.

SUMMARY OF THE INVENTION

The present invention provides particularly effective and efficient methods for refolding antibodies, particularly monoclonal antibodies, using high-pressure techniques (high hydrostatic pressure), as well as preparations of refolded monoclonal antibodies refolded using such high-pressure techniques. More specifically, the present invention is directed to high pressure refolding of monoclonal antibody aggregates produced after exposure to low pH. The methods provide routes for overcoming the difficulties in protein therapeutic processing, by employing the use of high pressure techniques. These methods allow for the disaggregation, refolding, and production of high quality antibodies, while circumventing problems that would otherwise be associated with therapeutic protein production. The methods advantageously provide processing benefits associated with the use of high pressure refolding of protein aggregates.

The basic method involves obtaining an antibody sample subsequent to incubation at low pH, for example, approximately pH 3.0 comprising a solution of antibody, exposing the antibody sample to high hydrostatic pressure for a period of time, and then reducing the hydrostatic pressure to atmospheric pressure, resulting in an antibody sample with a higher content of monomeric or properly refolded antibody than prior to the pressure exposure.

In one embodiment, the invention embraces a method for refolding a sample of an antibody, where the antibody sample comprises a solution of antibody exposed to low pH (such as pH 3). Such an antibody sample may still be at a solution condition of low pH, in which case, the pH of the solution is adjusted to above pH 5.0. The antibody sample is then exposed to high hydrostatic pressure for a period of time; subsequently, the pressure is reduced to atmospheric pressure. The antibody sample, after such pressure exposure, has a higher content of monomeric antibody, a higher content of properly folded antibody, or a lower content of aggregated antibody than the antibody sample prior to the pressure exposure. In one embodiment, the antibody sample after pressure exposure has a higher content of monomeric antibody than prior to pressure exposure. In one embodiment, the antibody sample after pressure exposure has a higher content of properly refolded antibody than prior to pressure exposure. In one embodiment, the antibody sample after pressure exposure has a lower content of aggregated antibody than prior to pressure exposure.

DETAILED DESCRIPTION OF THE INVENTION

All publications and patents mentions herein are hereby incorporated by reference in their respective entireties. The publications and patents disclosed herein are provided solely for their disclosure. Nothing herein is to be construed as an admission that the inventors are not entitled to antedate any publication and/or patent, including any publication and/or patent cited herein. U.S. Pat. Nos. 6,489,450 and 7,064,192, U.S. Patent Application Publication Nos. 2004/0038333 and 2006/0188970, and International Patent Application Publication No. WO 2007/062174 are specifically incorporated herein by reference in their entirety. In particular, the experimental techniques for refolding found in those documents are incorporated by reference herein.

The embodiments of the present invention described below are not intended to be exhaustive or to limit the invention to the precise forms disclosed in the following detailed description. Rather, the embodiments are chosen and described so that others skilled in the art can appreciated and understand the principles and practices of the present invention.

The methods of the present invention can be used to refold monoclonal antibodies, and are especially useful for the refolding of antibody aggregates produced after exposure to low pH. Unless otherwise stated, the following terms used in the specification and claims have the meaning(s) provided herein.

By "low pH" is meant solution conditions of about pH 1.0 to 5.0, preferably about pH 2.0 to about 4.0, more preferably about 2.5 to about 3.5, more preferably about 2.8 to about 3.2, more preferably about 3.0.

As used herein, a "protein aggregate" is defined as being composed of a multiplicity of protein molecules wherein non-native noncovalent interactions and/or non-native covalent bonds (such as non-native intermolecular disulfide bonds) hold the protein molecules together. Typically, but not always, an aggregate contains sufficient molecules so that it is insoluble; such aggregates are insoluble aggregates. There are also oligomeric proteins which occur in aggregates in solution; such aggregates are soluble aggregates. In addition, there is typically (but not always) a display of at least one epitope or region on the aggregate surface which is not displayed on the surface of native, non-aggregated protein. "Inclusion bodies" are a type of aggregate of particular interest to which the present invention is applicable. Other protein aggregates include, but are not limited to, soluble and insoluble precipitates, soluble non-native oligomers, gels, fibrils, films, filaments, protofibrils, amyloid deposits, plaques, and dispersed non-native intracellular oligomers.

"Atmospheric," "ambient," or "standard" pressure is defined as approximately 15 pounds per square inch (psi) or approximately 1 bar or approximately 100,000 Pascals.

"Biological activity" of a protein or polypeptide as used herein, means that the protein or polypeptide retains at least about 10% of maximal known specific activity as measured in an assay that is generally accepted in the art to be correlated with the known or intended utility of the protein. For proteins or polypeptides intended for therapeutic use, the assay of choice is one accepted by a regulatory agency to which data on safety and efficacy of the protein or polypeptide must be submitted. In some embodiments, a protein or polypeptide having at least about 10% of maximal known specific activity or of the non-denatured molecule is "biologically active" for the purposes of the invention. In some embodiments, the biological activity is at least about 15%, at least about 20%, at least about 25%, at least about 30%, at least about 40%, at least about 50%, at least about 75%, or at least about 90% of maximal known specific activity or of the non-denatured molecule.

"Denatured," as applied to a protein in the present context, means that native secondary, tertiary, and/or quaternary structure is disrupted to an extent that the protein does not have biological activity.

The "native conformation" of a protein refers to the secondary, tertiary and/or quaternary structures of a protein in its biologically active state.

"Refolding" in the present context means the process by which a fully or partially denatured polypeptide adopts secondary, tertiary and quaternary structure like that of the cognate native molecule. A properly refolded polypeptide has biological activity that is at least about 10% of the non-denatured molecule, preferably biological activity that is substantially that of the non-denatured molecule. In some embodiments, the biological activity is at least about 15%, at least about 20%, at least about 25%, at least about 30%, at least about 40%, at least about 50%, at least about 75%, or at least about 90% of the non-denatured molecule. Where the native polypeptide has disulfide bonds, oxidation to form native disulfide bonds is a desired component of the refolding process.

Antibodies which can be refolded with the methods of the invention include a wide variety of polyclonal or monoclonal preparations; monoclonal antibodies are the preferred antibody embodiment for refolding with the methods of the invention. The methods of the present invention are applicable to an antibody prepared via a typical process that may include exposure to low pH, e.g., pH 3.0, during preparation. Examples of antibodies which can be refolded with the methods of the invention, along with their indications, include, but are not limited to: Avastin® (bevacizumab, Genentech, Inc. South San Francisco, Calif.) for treatment of metastatic colorectal cancer and non-small cell lung cancer; Bexxar® (tositumomab, Smithkline Beecham Corp., Philadelphia Pa.) for treatment of non-Hodgkin's lymphoma; Campath® (alemtuzumab, Genzyme Corporation, Cambridge Mass.) for treatment of B-cell chronic lymphocytic leukemia; Erbitux® (cetuximab, ImClone Systems Inc., New York, N.Y.) for treatment of colorectal cancer; Herceptin® (trastuzumab, Genentech, Inc. South San Francisco, Calif.) for treatment of breast cancer; Humira® (adalimumab, Abbott Biotechnology Ltd., Hamilton Bermuda) for treatment of rheumatoid arthritis, psoriatic arthritis, ankylosing spondylitis, and Crohn's disease; Lucentis® (ranibizumab, Genentech, Inc. South San Francisco, Calif.) for treatment of wet age-related macular degeneration; Mylotarg® (gemtuzumab ozogamicin (antibody conjugated to antibiotic calicheamicin), Wyeth Corp., Madison, N.J.) for treatment of acute leukemia; Orencia® (abatacept; Bristol-Myers Squibb Co., New York, N.Y.) for treatment of rheumatoid arthritis; Orthoclone OKT3® (muromonab-CD3, Johnson & Johnson Corp., New Brunswick, N.J.) for treatment of transplant rejection; Raptiva® (efalizumab, Genentech, Inc. South San Francisco, Calif.) for treatment of plaque psoriasis; Remicade® (infliximab, Centocor, Inc., Malvern, Pa.) for treatment of rheumatoid arthritis, Crohn's disease, ankylosing spondylitis, psoriatic arthritis, plaque psoriasis, ulcerative colitis; ReoPro® (abciximab, Eli Lilly and Co., Indianapolis Ind.) as an adjunct to percutaneous coronary intervention; Rituxan® (rituximab, Biogen IDEC Inc., Cambridge Mass. and Genentech, Inc. South San Francisco, Calif.) for treatment of non-Hodgkin's lymphoma and rheumatoid arthritis; Simulect® (basiliximab, Novartis AG, Basel, Switzerland) for treatment of acute organ rejection; Soliris® (eculizumab, Alexion Pharmaceuticals, Inc., Cheshire, Conn.) for treatment of paroxysmal nocturnal hemoglobinuria; Synagis® (palivizumab, MedImmune, Inc., Gaithersburg, Md.) for treatment of respiratory syncytial virus; Tysabri® (natalizumab, Elan Pharmaceuticals, Inc., South San Francisco, Calif.) for treatment of multiple sclerosis; Vectibix® (panitumumab, Immunex Corp., Thousand Oaks, Calif.) for treatment of metastatic colorectal cancer; Xolair® (omalizumab, Novartis AG, Basel, Switzerland) for treatment of allergic asthma; Zenapax® (daclizumab, Roche Inc., Nutley, N.J.) for treatment of acute organ rejection; and Zevalin® (ibritumomab tiuxetan, Biogen IDEC Inc., Cambridge Mass.) for treatment of B-cell non-Hodgkin's lymphoma.

A wide variety of techniques are known in the art for protein separation and purification, such as affinity chromatography, high-pressure liquid chromatography (HPLC), dialysis, ion exchange chromatography, size exclusion chromatography, reverse-phase chromatography, ammonium sulfate precipitation, or electrophoresis. Several conditions for HPLC can be varied for enhancing separation, such as the stationary and mobile phases. HPLC can be used with ion-exchange columns, reverse-phase columns, affinity columns, size-exclusion columns, and other types of columns. FPLC, or "Fast Performance Liquid Chromatography," can also be used. Gel-filtration chromatography can be used at low solvent pressures. Removal of small molecules (such as chaotropes, kosmotropes, surfactants, detergents, reducing agents, oxidizing agents, or small molecule binding partners) from protein solutions can be achieved via diafiltration, ultrafiltration, or dialysis.

There are several assay methods for analyzing the monomeric/refolded content of antibody in a sample. A specific binding assay can be employed, to determine the degree of binding of the antibody to a specific binding partner. A binding assay measures the amount of active protein and is thus quite useful for determining the amount of functional protein.

Several methods based on physical parameters are available for analyzing and quantitating aggregated proteins, such as antibodies, and determining amounts of aggregated proteins and monomeric proteins. An excellent overview of several methods of analysis of macromolecules is found in Cantor, C. R. and P. R. Schimmel, *Biophysical Chemistry Part II:* *Techniques for the Study of Biological Structure and Function*, W.H. Freeman & Co., New York: 1980. Other general techniques are described in U.S. Patent Application Publication No. 2003/0022243.

The use of analytical ultracentrifugation for characterization of aggregation of protein therapeutics is specifically discussed in Philo, J. S., American Biotechnology Laboratory, page 22, October 2003. Experiments that can be performed using analytical ultracentrifugation include sedimentation velocity and sedimentation equilibrium experiments, which can be performed to determine whether multiple solutes exist in a solution (e.g., monomer, dimer, trimer, etc.) and provide an estimate of molecular weights for the solutes.

Size-exclusion chromatography and gel permeation chromatography can be used to estimate molecular weights and aggregation numbers of proteins, as well as for separation of different aggregates. See references such as Wu, C.-S. (editor), *Handbook of Size Exclusion Chromatography and Related Techniques, Second Edition (Chromatographic Science)*, Marcel Dekker: New York, 2004 (particularly chapter 15 at pages 439-462 by Baker et al., "Size Exclusion Chromatography of Proteins") and Wu, C.-S. (editor), *Column Handbook for Size Exclusion Chromatography*, San Diego: Academic Press, 1999 (particularly Chapters 2 and 18).

Field flow fractionation, which relies on a field perpendicular to a liquid stream of molecules, can also be used to analyze and separate aggregated proteins such as protein monomers, dimers, trimers, etc. See Zhu et al., Anal. Chem. 77:4581 (2005); Litzen et al., Anal. Biochem. 212:469 (1993); and Reschiglian et al., Trends Biotechnol. 23:475 (2005).

Light scattering methods, such as methods using laser light scattering (often in conjunction with size-exclusion chromatography or other methods) can also be used to estimate the molecular weight of proteins, including protein aggregates; see, for example, Mogridge, J., Methods Mol Biol. 261:113 (2004) and Ye, H., Analytical Biochem. 356:76 (2006). Dynamic light scattering techniques are discussed in Pecora, R., ed., *Dynamic Light Scattering: Applications of Photon Correlation Spectroscopy*, New York: Springer Verlag, 2003 and Berne, B. J. and Pecora, R., *Dynamic Light Scattering: With Applications to Chemistry, Biology, and Physics*, Mineola, N.Y.: Dover Publications, 2000. Laser light scattering is discussed in Johnson, C. S. and Gabriel, D. A., Laser Light Scattering, Mineola, N.Y.: Dover Publications, 1995, and other light scattering techniques which can be applied to determine protein aggregation are discussed in Kratochvil, P., *Classical Light Scattering from Polymer Solutions*, Amsterdam: Elsevier, 1987.

Light obscuration can also be used to measure protein aggregation; see Seefeldt et al., Protein Sci. 14:2258 (2005); Kim et al., J. Biol. Chem. 276: 1626 (2001); and Kim et al., J. Biol. Chem. 277: 27240 (2002).

Fluorescence spectroscopy, such as fluorescence anisotropy spectroscopy, can be used to determine the presence of protein aggregates. Fluorescence probes (dyes) can be covalently or non-covalently bound to the aggregate to aid in analysis of aggregates (see, e.g., Lindgren et al., Biophys. J. 88: 4200 (2005)), U.S. Patent Application Publication 2003/0203403), or Royer, C. A., Methods Mol. Biol. 40:65 (1995). Internal tryptophan residues can also be used to detect protein aggregation; see, e.g., Dusa et al., Biochemistry 45:2752 (2006).

Many methods of gel electrophoresis can be employed to analyze proteins and protein aggregation. One of the most common methods of gel electrophoresis is polyacrylamide gel electrophoresis (PAGE). If an aggregate is covalently linked, denaturing PAGE (using, e.g., sodium dodecyl sulfate) can be employed. Native PAGE (non-denaturing PAGE) can be used to study non-covalently linked aggregates. See, e.g., Hermeling et al. *J. Phar. Sci.* 95:1084-1096 (2006); Kilic et al., Protein Sci. 12:1663 (2003); Westermeier, R., *Electrophoresis in Practice: A Guide to Methods and Applications of DNA and Protein Separations* 4$^{th}$ edition, New York: John Wiley & Sons, 2005; and Hames, B. D. (Ed.), *Gel Electrophoresis of Proteins: A Practical Approach*, 3$^{rd}$ edition, New York: Oxford University Press, USA, 1998.

Gas-phase electrophoretic mobility molecular analysis (GEMMA) (see Bacher et al., J. Mass Spectrom. 36:1038 (2001), Kaufman et al., Anal. Chem. 68:1895 (1996) and Kaufman et al., Anal. Biochem. 259:195 (1998)), a combination of electrophoresis in the gas phase and mass spectrometry, provides another method of analyzing protein complexes and aggregates.

Nuclear magnetic resonance spectroscopic techniques can be used to estimate hydrodynamic parameters related to protein aggregation. See, for example, James, T. L. (ed.), *Nuclear Magnetic Resonance of Biological Macromolecules, Part C, Volume* 394: *Methods in Enzymology*, San Diego: Academic Press, 2005; James, T. L., Dotsch, V. and Schmitz, U. (eds.), *Nuclear Magnetic Resonance of Biological Macromolecules, Part A* (*Methods in Enzymology, Volume* 338) and *Nuclear Magnetic Resonance of Biological Macromolecules, Part B* (*Methods in Enzymology, Volume* 339), San Diego: Academic Press, 2001, and Mansfield, S. L. et al., J. Phys. Chem. B, 103:2262 (1999). Linewidths, correlation times, and relaxation times are among the parameters that can be measured to estimate tumbling time in solution, which can then be correlated with the state of protein aggregation. Electron paramagnetic resonance (EPR or ESR) can also be used to determine aggregation states; see, e.g., Squier et al., J. Biol. Chem. 263:9162 (1988).

Reverse-phase high-pressure liquid chromatography (RP-HPLC) can also be used to determine monomer/aggregate content of protein preparations, although this method must be used cautiously, as the conditions used for RP-HPLC may alter the amount of aggregate present in the original sample.

In one embodiment of the invention, analytical ultracentrifugation is used for the comparison of aggregates in pressure-treated and untreated samples. In another embodiment of the invention, size exclusion chromatography is used for the comparison of aggregates in pressure-treated and untreated samples. In another embodiment of the invention, field flow fractionation is used for the comparison of aggregates in pressure-treated and untreated samples. In another embodiment of the invention, light scattering analysis is used for the comparison of aggregates in pressure-treated and untreated samples. In another embodiment of the invention, light obscuration analysis is used for the comparison of aggregates in pressure-treated and untreated samples. In another embodiment of the invention, fluorescence spectroscopy is used for the comparison of aggregates in pressure-treated and untreated samples. In another embodiment of the invention, gel electrophoresis is used for the comparison of aggregates in pressure-treated and untreated samples. In another embodiment of the invention, GEMMA is used for the comparison of aggregates in pressure-treated and untreated samples. In another embodiment of the invention, nuclear magnetic resonance spectroscopy is used for the comparison of aggregates in pressure-treated and untreated samples. In another embodiment of the invention, electron paramagnetic resonance spectroscopy is used for the comparison of aggregates in pressure-treated and untreated samples. In another embodiment of the invention, reverse-phase chromatography is used for the comparison of aggregates in pressure-treated and untreated samples.

Several conditions can be adjusted for optimal protein refolding: protein concentration; agitation; temperature; reduction of pressure and combinations thereof.

The concentration of protein can be adjusted for optimal protein refolding. One advantage of high-pressure protein refolding is that much higher concentrations of protein can be used as compared to chemical refolding techniques. Protein concentrations of at least about 0.1 mg/ml, at least about 1.0 mg/ml, at least about 5.0 mg/ml, at least about 10 mg/ml, or at least about 20 mg/ml can be used. Protein in the sample may be present in a concentration of from about 0.001 mg/ml to about 300 mg/ml. Thus, in some embodiments the protein is present in a concentration of from about 0.001 mg/ml to about 250 mg/ml, from about 0.001 mg/ml to about 200 mg/ml, from about 0.001 mg/ml to about 150 mg/ml, from about 0.001 mg/ml to about 100 mg/ml, from about 0.001 mg/ml to about 50 mg/ml, from about 0.001 mg/ml to about 30 mg/ml, from about 0.05 mg/ml to about 300 mg/ml, from about 0.05 mg/ml to about 250 mg/ml, from about 0.05 mg/ml to about 200 mg/ml, from about 0.05 mg/ml to about 150 mg/ml, from about 0.05 mg/ml to about 100 mg/ml, from about 0.05 mg/ml to about 50 mg/ml, from about 0.05 mg/ml to about 30 mg/ml, from about 10 mg/ml to about 300 mg/ml, from about 10 mg/ml to about 250 mg/ml, from about 10 mg/ml to about 200 mg/ml, from about 10 mg/ml to about 150 mg/ml, from about 10 mg/ml to about 100 mg/ml, from about 10 mg/ml to about 50 mg/ml, from about 10 mg/ml to about 30 mg/ml, from about 0.1 mg/ml to about 100 mg/ml, from about 0.1 mg/ml to about 10 mg/ml, from about 1 mg/ml to about 100 mg/ml, from about 1 mg/ml to about 10 mg/ml, from about 10 mg/ml to about 100 mg/ml, or from about 50 mg/ml to about 100 mg/ml can be used.

As used in the present context the phrase "a period of time sufficient to form biologically active protein" and cognates thereof refer to the time needed for the protein aggregates to be disaggregated and to adopt a conformation where the protein is biologically active. Typically, the time sufficient for solubilization is about 15 minutes to about 50 hours, or possibly longer depending on the particular protein, (e.g., as long as necessary for the protein; for example, up to about 1 week, about 5 days, about 4 days, about 3 days, etc.). Thus, in some embodiments of the methods, the time sufficient for formation of biologically active protein may be from about 2 to about 30 hours, from about 2 to about 24 hours, from about 2 to about 18 hours, from about 1 to about 10 hours, from about 1 to about 8 hours, from about 1 to about 6 hours, from about 2 to about 10 hours, from about 2 to about 8 hours, from about 2 to about 6 hours, or about 2 hours, about 6 hours, about 10 hours, about 16 hours, about 20 hours, or about 30 hours, from about 2 to about 10 hours, from about 2 to about 8 hours, from about 2 to about 6 hours, from about 12 to about 18 hours, or from about 10 to about 20 hours.

The sample comprising protein aggregates or denatured protein is typically an aqueous solution or aqueous suspension. The sample may also include other components. These additional components may be one or more additional agents including: one or more stabilizing agents, one or more buffering agents, one or more surfactants, one or more salts, one or more chaotropes, or combinations of two or more of the foregoing.

The amounts of the additional agents will vary depending on the selection of the protein, however, the effect of the presence (and amount) or absence of each additional agent or combinations of agents can be determined and optimized using the teachings provided herein.

Exemplary additional agents include, but are not limited to, buffers (examples include, but are not limited to, phosphate buffer, borate buffer, carbonate buffer, citrate buffer, HEPES, MEPS), salts (examples include, but are not limited to, the chloride, sulfate, and carbonate salts of sodium, zinc, calcium, ammonium and potassium), chaotropes (examples include, but are not limited to, urea, guanidine hydrochloride, guanidine sulfate and sarcosine), and stabilizing agents (e.g., preferential excluding compounds, etc.).

Non-specific protein stabilizing agents act to favor the most compact conformation of a protein. Such agents include, but are not limited to, one or more free amino acids, one or more preferentially excluding compounds, kosmotropes, trimethylamine oxide, cyclodextrans, molecular chaperones, and combinations of two or more of the foregoing.

Amino acids can be used to prevent reaggregation and facilitate the dissociation of hydrogen bonds. Typical amino acids that can be used, but not limited to, are arginine, lysine, proline, glycine, histidine, and glutamine or combinations of two or more of the foregoing. In some embodiments, the free amino acid(s) is present in a concentration of about 0.1 mM to about the solubility limited of the amino acid, and in some variations from about 0.1 mM to about 2 M. The optimal concentration is a function of the desired protein and should favor the native conformation.

Preferentially excluding compounds can be used to stabilize the native confirmation of the protein of interest. Possible preferentially excluding compounds include, but are not limited to, sucrose, hexylene glycol, sugars (e.g., sucrose, trehalose, dextrose, mannose), and glycerol. The range of concentrations that can be use are from 0.1 mM to the maximum concentration at the solubility limit of the specific compound. The optimum preferential excluding concentration is a function of the protein of interest.

In particular embodiments, the preferentially excluding compound is one or more sugars (e.g., sucrose, trehalose, dextrose, mannose or combinations of two or more of the foregoing). In some embodiments, the sugar(s) is present in a concentration of about 0.1 mM to about the solubility limit of the particular compound. In some embodiments, the concentration is from about 0.1 mM to about 2M, from about 0.1 mM to about 1.5M, from about 0.1 mM to about 1M, from about 0.1 mM to about 0.5M, from about 0.1 mM to about 0.3M, from about 0.1 mM to about 0.2M, from about 0.1 mM to about 0.1 mM, from about 0.1 mM to about 50 mM, from about 0.1 mM to about 25 mM, or from about 0.1 mM to about 10 mM. When present as a percentage of solution (w/w and/or w/v), the concentration can be about 0.1% to about 20%, about 1% to about 20%, about 1% to about 15%, about 5% to about 20%, about 5% to about 15%, about 8% to about 12%, or about 10%.

In some embodiments, the stabilizing agent is one or more of sucrose, trehalose, glycerol, betaine, amino acid(s), or trimethylamine oxide.

In certain embodiments, the stabilizing agent is a cyclodextran. In some embodiments, the cyclodextran is present in a concentration of about 0.1 mM to about the solubility limit of the cyclodextran. In some variations, the cyclodextran is present in a concentration from about 0.1 mM to about 2 M.

In certain embodiments, the stabilizing agent is a molecular chaperone. In some embodiments, the molecular chaperone is present in a concentration of about 0.01 mg/ml to 10 mg/ml.

A single stabilizing agent maybe be used or a combination of two or more stabilizing agents (e.g., at least two, at least three, or 2 or 3 or 4 stabilizing agents). Where more than one stabilizing agent is used, the stabilizing agents may be of different types, for example, at least one preferentially excluding compound and at least one free amino acid, at least one preferentially excluding compound and betaine, etc.

Buffering agents may be present to maintain a desired pH value or pH range. Numerous suitable buffering agents are known to the skilled artisan and should be selected based on the pH that favors (or which does not disfavor) the native conformation of the protein of interest. Either inorganic or organic buffering agents may be used. Suitable concentrations are known to the skilled artisan and should be optimized for the methods as described herein according to the teaching provided based on the characteristics of the desired protein.

Thus, in some embodiments, at least one inorganic buffering agent is used (e.g., phosphate, carbonate, etc.). In certain embodiments, at least one organic buffering agent is used (e.g., citrate, acetate, Tris, MOPS, MES, HEPES, etc.) Additional organic and inorganic buffering agents are well known to the art.

In some embodiments, the one or more buffering agents is phosphate buffer, borate buffer, carbonate buffer, citrate buffer, HEPES, MEPS, MOPS, MES, or acetate buffer.

In some embodiments, the one or more buffering agents is phosphate buffers, carbonate buffers, citrate, Tris, MOPS, MES, acetate or HEPES.

A single buffering agent maybe be used or a combination of two or more buffering agents (e.g., at least two, at least 3, or 2 or 3 or 4 buffering agents).

A "surfactant" as used in the present context is a surface active compound which reduces the surface tension of water.

Surfactants are used to improve the solubility of certain proteins. Surfactants should generally be used at concentrations above or below their critical micelle concentration (CMC), for example, from about 5% to about 20% above or below the CMC. However, these values will vary dependent upon the surfactant chosen, for example, surfactants such as, beta-octylgluco-pyranoside may be effective at lower concentrations than, for example, surfactants such as TWEEN-20 (polysorbate 20). The optimal concentration is a function of each surfactant, which has its own CMC.

Useful surfactants include nonionic (including, but not limited to, t-octylphenoxypolyethoxy-ethanol and polyoxyethylene sorbitan), anionic (e.g., sodium dodecyl sulfate) and cationic (e.g., cetylpyridinium chloride) and amphoteric agents. Suitable surfactants include, but are not limited to deoxycholate, sodium octyl sulfate, sodium tetradecyl sulfate, polyoxyethylene ethers, sodium cholate, octylthioglucopyranoside, n-octylglucopyranoside, alkyltrimethylammonium bromides, alkyltrimethyl ammonium chlorides, and sodium bis (2 ethylhexyl) sulfosuccinate. In some embodiments the surfactant may be polysorbate 80, polysorbate 20, sarcosyl, Triton X-100, β-octyl-gluco-pyranoside, or Brij 35.

In some embodiments the one or more surfactant may be a polysorbate, polyoxyethylene ether, alkyltrimethylammonium bromide, pyranosides or combination of two or more of the foregoing. In certain embodiments, the one or more surfactant may be β-octyl-gluco-pyranoside, Brij 35, or a polysorbate.

In certain embodiments the one or more surfactant may be octyl phenol ethoxylate, β-octyl-gluco-pyranoside, polyoxyethyleneglycol dodecyl ether, sarcosyl, sodium dodecyl sulfate, polyethoxysorbitan, deoxycholate, sodium octyl sulfate, sodium tetradecyl sulfate, sodium cholate, octylthioglucopyranoside, n-octylglucopyranoside, sodium bis(2-ethylhexyl) sulfosuccinate or combinations of two or more of the foregoing. A single surfactant maybe be used or a combination of two or more surfactants (e.g., at least two, at least 3, or 2 or 3 or 4 surfactants).

Chaotropic agents (also referred to as a "chaotrope") are compounds, including, without limitation, guanidine, guanidine hydrochloride (guanidinium hydrochloride, GdmHCl), guanidine sulfate, urea, sodium thiocyanate, and/or other compounds which disrupt the noncovalent intermolecular bonding within the protein, permitting the polypeptide chain to assume a substantially random conformation.

Chaotropic agents may be used in concentration of from about 10 mM to about 8 M. The optimal concentration of the chaotropic agent will depend on the desired protein as well as on the particular chaotropes selected. The choice of particular chaotropic agent and determination of optimal concentration can be optimized by the skilled artisan in view of the teachings provided herein.

In some embodiments, the concentration of the chaotropic agent will be, for example, from about 10 mM to about 8 M, from about 10 mM to about 7 M, from about 10 mM to about 6 M, from about 0.1 M to about 8 M, from about 0.1 M to about 7 M, from about 0.1 M to about 6 M, from about 0.1 M to about 5 M, from about 0.1 M to about 4 M, from about 0.1 M to about 3 M, from about 0.1 M to about 2 M, from about 0.1 M to about 1 M, from about 10 mM to about 4 M, from about 10 mM to about 3 M, from about 10 mM to about 2 M, from about 10 mM to about 1 M, or about, 10 mM, about 50 mM, about 75 mM, about 0.1 M, about 0.5 M, about 0.8 M, about 1 M, about 2 M, about 3 M, about 4 M, about 5 M, about 6 M, about 7 M, or about 8 M.

When used in the present methods, it is often advantageous to use chaotropic agents in non-denaturing concentrations to facilitate the dissociation of non-covalent interactions. While a non-denaturing concentration will vary depending on the desired protein, the range of non-denaturing concentrations is typically from about 0.1 to about 4 M. In some embodiments the concentration is from about 0.1 M to about 2 M.

In certain embodiments, guanidine hydrochloride or urea are the chaotropic agents.

A single chaotropic agent maybe be used or a combination of two or more chaotropic agents (e.g., at least two, at least 3, or 2 or 3 or 4 chaotropic agents).

Agitation is another aspect that may be manipulated. Protein solutions can be agitated before and/or during refolding. Agitation can be performed by methods including, but not limited to, ultrasound energy (sonication), mechanical stirring, mechanical shaking, pumping through mixers, or via cascading solutions. Agitation may be performed for any length of time, such as the entire period of high-pressure treatment, or for one or more periods of about 1 to about 60 minutes during high-pressure treatment, such as about 1 minute, about 5 minutes, about 10 minutes, about 20 minutes, about 30 minutes, about 45 minutes, or about 60 minutes.

Yet another aspect that may be manipulated is temperature. The methods described herein can be performed at a range of temperature values, depending on the particular protein of interest. The optimal temperature, in concert with other factors, can be optimized as described herein. Proteins can be refolded at various temperatures, including at about room temperature, about 20° C., about 25° C., about 30° C., about 37° C., about 50° C., about 75° C., about 100° C., about 125° C., or ranges of from about 20 to about 125° C., about 25 to about 125° C., about 25 to about 100° C., about 25 to about 75° C., about 25 to about 50° C., about 50 to about 125° C., about 50 to about 100° C., about 50 to about 75° C., about 75 to about 125° C., about 5 to about 100° C., or about 100 to about 125° C.

In some embodiments of the methods, the temperature can range from about 0° C. to about 100° C. without adversely affecting the protein of interest. Thus in certain embodiments, the temperature may be from about 0° C. to about 75° C., from about 0° C. to about 55° C., from about 0° C. to about 35° C., from about 0° C. to about 25° C., from about 20° C. to about 75° C., from about 20° C. to about 65° C., from about 20° C. to about 35° C., or from about 20° C. to about 25° C.

Although increased temperatures are often used to cause aggregation of proteins, when coupled with increased hydrostatic pressure it has been found that increased temperatures can enhance refolding recoveries effected by high pressure treatment, provided that the temperatures are not so high as to cause irreversible denaturation. Generally, the increased temperature for refolding should be about 20° C. lower than the temperatures at which irreversible loss of activity occurs. Relatively high temperatures (for example, about 60° C. to about 125° C., about 80° C. to about 110° C., including about 100° C., about 105° C., about 110° C., about 115° C., about 120° C. and about 125° C.) may be used while the solution is under pressure, as long as the temperature is reduced to a suitably low temperature before depressurizing. Such a suitably low temperature is defined as one below which thermally-induced denaturation or aggregation occurs at atmospheric conditions.

"High pressure" or "high hydrostatic pressure," for the purposes of the invention is defined as pressures of from about 500 bar to about 10,000 bar.

In some embodiments, the increased hydrostatic pressure may be from about 500 bar to about 5000 bar, from about 500 bar to about 4000 bar, from about 500 bar to about 2000 bar, from about 500 bar to about 2500 bar, from about 500 bar to about 3000 bar, from about 500 bar to about 6000 bar, from about 1000 bar to about 5000 bar, from about 1000 bar to about 4000 bar, from about 1000 bar to about 2000 bar, from about 1000 bar to about 2500 bar, from about 1000 bar to about 3000 bar, from about 1000 bar to about 6000 bar, from about 1500 bar to about 5000 bar, from about 1500 bar to about 3000 bar, from about 1500 bar to about 4000 bar, from about 1500 bar to about 2000 bar, from about 2000 bar to about 5000 bar, from about 2000 bar to about 4000 bar, from about 2000 bar to about 3000 bar, or about 1000 bar, about 1500 bar, about 2000 bar, about 2500 bar, about 3000 bar, about 3500 bar, about 4000 bar, about 5000 bar, about 6000 bar, about 7000 bar, about 8000 bar, or about 9000 bar.

Reduction of pressure is another parameter that can be manipulated. Where the reduction in pressure is performed in a continuous manner, the rate of pressure reduction can be constant or can be increased or decreased during the period in which the pressure is reduced. In some variations, the rate of pressure reduction is from about 5000 bar/1 sec to about 5000 bar/4 days (or about 3 days, about 2 days, or about 1 day). Thus in some variations the rate of pressure reduction can be performed at a rate of from about 5000 bar/1 sec to about 5000 bar/80 hours, from about 5000 bar/1 sec to about 5000 bar/72 hours, from about 5000 bar/1 sec to about 5000 bar/60 hours, from about 5000 bar/1 sec to about 5000 bar/50 hours, from about 5000 bar/1 sec to about 5000 bar/48 hours, from about 5000 bar/1 sec to about 5000 bar/32 hours, from about 5000 bar/1 sec to about 5000 bar/24 hours, from about 5000 bar/1 sec to about 5000 bar/20 hours, from about 5000 bar/1 sec to about 5000 bar/18 hours, from about 5000 bar/1 sec to about 5000 bar/16 hours, from about 5000 bar/1 sec to about 5000 bar/12 hours, from about 5000 bar/1 sec to about 5000 bar/8 hours, from about 5000 bar/1 sec to about 5000 bar/4 hours, from about 5000 bar/1 sec to about 5000 bar/2 hours, from about 5000 bar/1 sec to about 5000 bar/1 hour, from about 5000 bar/1 sec to about 1000 bar/min, about 5000 bar/1 sec to about 500 bar/min, about 5000 bar/1 sec to about 300 bar/min, about 5000 bar/1 sec to about 250 bar/min, about 5000 bar/1 sec to about 200 bar/min, about 5000 bar/1 sec to about 150 bar/min, about 5000 bar/1 sec to about 100, about 5000 bar/1 sec to about 80 bar/min, about 5000 bar/1 sec to about 50 bar/min, or about 5000 bar/1 sec to about 10 bar/min. For example, about 10 bar/min, about 250 bar/5 minute, about 500 bar/5 minutes, about 1000 bar/5 minutes, about 250 bar/5 minutes, 2000 bar/50 hours, 3000 bar/50 hours, 40000 bar/50 hours, etc. In some embodiments, the pressure reduction may be approximately instantaneous, as in where pressure is released by simply opening the device in which the sample is contained and immediately releasing the pressure.

Where the reduction in pressure is performed in a stepwise manner, the process comprises dropping the pressure from the highest pressure used to at least a secondary level that is intermediate between the highest level and atmospheric pressure. The goal is to provide a hold period at or about this intermediate pressure zone that permits a protein to adopt a desired conformation.

In some embodiments, where there are at least two stepwise pressure reductions there may be a hold period at a constant pressure between intervening steps. The hold period may be from about 10 minutes to about 50 hours (or longer, depending on the nature of the protein of interest). In some embodiments, the hold period may be from about 2 to about 30 hours, from about 2 to about 24 hours, from about 2 to about 18 hours, from about 1 to about 10 hours, from about 1 to about 8 hours, from about 1 to about 6 hours, from about 2 to about 10 hours, from about 2 to about 8 hours, from about 2 to about 6 hours, or about 2 hours, about 6 hours, about 10 hours, about 20 hours, or about 30 hours, from about 2 to about 10 hours, from about 2 to about 8 hours, or from about 2 to about 6 hours.

In some variations, the pressure reduction includes at least 2 stepwise reductions of pressure (e.g., highest pressure reduced to a second pressure reduced atmospheric pressure would be two stepwise reductions). In other embodiments the pressure reduction includes more than 2 stepwise pressure reductions (e.g., 3, 4, 5, 6, etc.). In some embodiments, there is at least 1 hold period. In certain embodiments there is more than one hold period (e.g., at least 2, at least 3, at least 4, at least 5 hold periods).

In some variations of the methods the constant pressure after an initial stepwise reduction may be at a hydrostatic pressure of from about 500 bar to about 5000 bar, from about 500 bar to about 4000 bar, from about 500 bar to about 2000 bar, from about 1000 bar to about 4000 bar, from about 1000 bar to about 3000 bar, from about 1000 bar to about 2000 bar, from about 1500 bar to about 4000 bar, from about 1500 bar to about 3000 bar, from about 2000 bar to about 4000 bar, or from about 2000 bar to about 3000 bar.

In particular variations, constant pressure after the stepwise reduction is from about four-fifths of the pressure immediately prior to the stepwise pressure reduction to about one-tenth of prior to the stepwise pressure reduction. For example, constant pressure is at a pressure of from about four-fifths to about one-fifth, from about two-thirds to about one-tenth, from about two-thirds to about one-fifth, from about two-thirds to about one-third, about one-half, or about one-quarter of the pressure immediately prior to the stepwise pressure reduction. Where there is more than one stepwise pressure reduction step, the pressure referred to is the pressure immediately before the last pressure reduction (e.g., where 2000 bar is reduced to 1000 bar is reduced to 500 bar, the pressure of 500 bar is one-half of the pressure immediately preceding the previous reduction (1000 bar)).

Where the pressure is reduced in a stepwise manner, the rate of pressure reduction (e.g., the period of pressure reduction prior to and after the hold period) may be in the same range as that rate of pressure reduction described for continuous reduction (e.g., in a non-stepwise manner). In essence, stepwise pressure reduction is the reduction of pressure in a continuous manner to an intermediate constant pressure, followed by a hold period and then a further reduction of pressure in a continuous manner. The periods of continuous pressure reduction prior to and after each hold period may be the same continuous rate for each period of continuous pressure reduction or each period may have a different reduction rate. In some variations, there are two periods of continuous pressure reduction and a hold period. In certain embodiments, each continuous pressure reduction period has the same rate of pressure reduction. In other embodiments, each period has a different rate of pressure reduction. In particular embodiments, the hold period is from about 8 to about 24 hours. In some embodiments, the hold period is from about 12 to about 18 hours. In particular embodiments, the hold period is about 16 hours.

Various combinations and permutations of the condition above, such as agitation of the protein under high pressure at an elevated temperature in the presence of chaotropes and redox reagents, can be employed as desired for optimization of refolding yields.

Optimization of reaction conditions for solubilization and refolding in the context of the methods described herein are a function of the characteristics of both the target antibody and any other components or parameters of the solution. In standard optimization experiments, the influence of pressure, pH, temperature, ionic strength, surfactants, chaotropes, stabilizing agents, and refolding time on refolding should be tested. Once the key process parameters are identified, a central composite design can be used to optimize the appropriate conditions for each parameter. Guidance regarding typical ranges for the various parameters is provided in more detail below.

Initial studies can be conducted to screen the effect of solution conditions, solution pH, and high pressure treatment on the solubilization and/or refolding of proteins. Screening studies are typically conducted, but not limited to, empirical screens that examine step-wise the effect of processing conditions on yields. Synergistic effects between different parameters are not examined in these screening studies. Exemplary screening studies that can be conducted are as described for the cases of recombinant placental bikunin, recombinant growth hormone, and malaria pfs48 (see e.g., Seefeldt et al. *Protein Science*, v13 (10), 2639-2650 2004, St. John et al., *Journal of Biological Chemistry*, v276 (50), 46856-46864, 2001, Seefeldt, "High pressure refolding of protein aggregates: efficacy and thermodynamics," *Dept. of Chemical and Biological Engineering Thesis*, (2004), the disclosures of which are herein incorporated by reference in their entirety, particularly with respect to the screening studies described therein). High pressure refolding studies of bikunin and growth hormone demonstrate the step-wise screening process for solution conditions (pH 5-9), temperature (0-60° C.), ionic strength (0-160 mM NaCl), non-denaturing concentrations of chaotropes (0-1.0 M urea or 0-2.0 M guanidine) and refolding time (0-24 hours). Studies can be conducted at about 2000 bar, about 2100 bar, about 2150 bar, etc. and compared to samples treated at atmospheric pressure. Other parameters, including those described herein, that can be screened include, but are not limited to, the presence and amount of stabilizing agents, surfactants, salts, etc., as described herein. It should be noted that statistical analysis of variance (ANOVA's) can be used to rapidly screen which solution parameters affect refolding yields. In addition to the teaching provided herein, U.S. 2004/0038333, Seefeldt et al. *Protein Science*, v13 (10), 2639-2650 2004, and St. John et al., *Biotechnology Progress*, v18, (3), 565-571, 2002 (incorporated herein by reference in their entirety) also provide guidance regarding empirical screening procedures for determining the optimal solubilization and refolding conditions.

In this manner, the skilled artisan can determine the effect of processing conditions on the refolding of protein aggregates through the use of high pressure. It has been shown in the literature that refolding reactions can have interactions between the process conditions, which prevents single-variable screening from effectively optimizing the process. For instance, pH affects protein conformation stability, protein colloidal stability, and disulfide bond formation kinetics. To effectively optimize the effect of pH, or any other process parameter, studies need to be conducted to account for interactions. In these instances, statistical experimental designs need to be employed. As described herein, solubilization is also examined as a function of urea, by step-wise analysis in a range from 0-4.5 M urea at pH 8.0. Once the significant parameters are identified, a face-centered statistical designed experiment is used to optimize the refolding conditions, taking into account interactions.

After initial optimization studies are performed for the protein of interest, more granular optimization can be used to determine the optimal conditions for performing the solubilization and refolding processes. This process can generally be described as an experimental optimization that takes into account synergistic interactions between the critical parameters identified in the initial step-wise studies. An effective method for conducting these studies involves using a three or five level central composite statistical analysis, which takes into account interactions between the reaction parameters while minimizing the required number of experiments.

Another useful aid for optimizing conditions and/or monitoring solubilization or refolding is in situ spectroscopic measurement of samples under pressure, a well-known process for examining polypeptide stability under pressure. Using high pressure spectroscopic techniques to observe aggregate dissolution under pressure will help determine the optimal pressure ranges for recovering proteins from aggregates. Custom made high pressure cells have been routinely used for high pressure unfolding studies and can be adapted for use in high pressure disaggregation and refolding. Additional guidance for the skilled artisan may also be found in Paladini and Weber, *Biochemistry*, 20 (9), 2587-2593 (1981) and Seefeldt et al. *Protein Science*, 13 (10), 2639-2650 (2004), incorporated by reference herein in their entirety.

Methods that can be employed to monitor the optimization of various parameters include Fourier Transform Infrared Spectroscopy (FTIR), circular dichroism (CD) spectroscopy (far and/or near UV), UV spectroscopy, measurement of total protein concentrations (e.g., BCA assay method (Pierce Chemical Co., Rockford, Ill.), etc), activity assays to measure the activity of the target polypeptide, electrophoretic gels with molecular weight markers to visualize the appearance of native protein under various conditions, HPLC analysis of soluble polypeptide fractions, etc.

Suitable devices for performing high pressure spectroscopy can be obtained commercially (e.g., such as fluorescence cells available from ISS Inc., Champaign, Ill. or fluo-rescence/ultraviolet absorbance cells available from BaroFold Inc., Boulder, Colo.) or can be fabricated by the skilled artisan. For example, Randolph et al., U.S. Patent Application Publication No. 2004/0038333, incorporated by reference herein in its entirety, described a high-pressure W spectroscopy cell made of stainless steel, sealed with Btma-N 90 durometer o-rings and with an optical port diameter of 6 mm and pathlength of 7.65 mm. The cell utilized cylindrical sapphire windows (16 mm diameter, 5.1 mm thick) and was capable of experiments up to 250 MPa. Separation of the sample from the pressure transmitting fluid was facilitated by a piston device external to the cell.

Commercially available high pressure devices and reaction vessels, such as those described in the examples, may be used to achieve the hydrostatic pressures in accordance with the methods described herein (see BaroFold Inc., Boulder, Colo.). Additionally devices, vessels and other materials for carrying out the methods described herein, as well as guidance regarding the performing increased pressure methods, are described in detail in U.S. Pat. No. 6,489,450, which is incorporated herein in its entirety. The skilled artisan is particularly directed to column 9, lines 39-62 and Examples 2-4. International Pat. App. Pub. No. WO 02/062827, incorporated herein in its entirety, also provides the skilled artisan with detailed teachings regarding devices and use thereof for high hydrostatic pressure solubilization of aggregates throughout the specification. Particular devices and teachings regarding the use of high pressure devices are also provided in International Patent Application Publication No. WO 2007/062174, which is incorporated by reference herein in its entirety.

Multiple-well sample holders may be used and can be conveniently sealed using self-adhesive plastic covers. The containers, or the entire multiple-well sample holder, may then be placed in a pressure vessel, such as those commercially available from the Flow International Corp. or High Pressure Equipment Co. The remainder of the interior volume of the high-pressure vessel may than be filled with water or other pressure transmitting fluid.

Mechanically, there are two primary methods of high-pressure processing: batch and continuous. Batch processes simply involve filling a specified chamber, pressurizing the chamber for a period of time, and depressurizing the batch. In contrast, continuous processes constantly feed aggregates into a pressure chamber and soluble, refolded proteins move out of the pressure chamber. In both set ups, good temperature and pressure control is essential, as fluctuations in these parameters can cause inconsistencies in yields. Both temperature and pressure should be measured inside the pressure chamber and properly controlled.

There are many methods for handling batch samples depending upon the specific stability issues of each target protein. Samples can be loaded directly into a pressure chamber, in which case the aqueous solution and/or suspension would be used as the pressure medium.

Alternately, samples can be loaded into any variety of sealed, flexible containers, including those described herein. This allows for greater flexibility in the pressure medium, as well as the surfaces to which the sample is exposed. Sample vessels could conceivably even act to protect the desired protein from chemical degradation (e.g., oxygen scavenging plastics are available).

With continuous processing, small volumes under pressure can be used to refold large volumes of the sample. In addition, using an appropriate filter on the outlet of a continuous process will selectively release soluble desired protein from the chamber while retaining both soluble and insoluble aggregates.

Pressurization is a process of increasing the pressure (usually from atmospheric or ambient pressure) to a higher pressure. Pressurization takes place over a predetermined period of time, ranging from 0.1 second to 10 hours. Such times include 1 second, 2 seconds, 5 seconds, 10 seconds, 20 seconds, 1 minute, 2 minutes, 5 minutes, 10 minutes, 30 minutes, 60 minutes, 2 hours, 3 hours, 4 hours, and 5 hours.

Depressurization is a process of decreasing the pressure, from a high pressure, to a lower pressure (usually atmospheric or ambient pressure). Depressurization takes place over a predetermined period of time, ranging from 10 seconds to 10 hours, and may be interrupted at one or more points to permit optimal refolding at intermediate (but still increased compared to ambient) pressure levels. The depressurization or interruptions may be 1 second, 2 seconds, 5 seconds, 10 seconds, 20 seconds, 1 minute, 2 minutes, 5 minutes, 10 minutes, 30 minutes, 60 minutes, 2 hours, 3 hours, 4 hours, and 5 hours.

Degassing is the removal of gases dissolved in solutions and is often advantageous in the practice of the methods described herein. Gas is much more soluble in liquids at high pressure as compared to atmospheric pressure and, consequently, any gas headspace in a sample will be driven into solution upon pressurization. The consequences are two-fold: the additional oxygen in solution may chemically degrade the protein product, and gas exiting solution upon repressurization may cause additional aggregation. Thus, samples should be prepared with degassed solutions and all headspace should be filled with liquid prior to pressurization.

EXAMPLES

Example 1

Use of High Pressure to Disaggregate and Refold Aggregates of Orencia® (CTLA-4Ig; Abatacept)

Aggregation states of Orencia® (Orencia® is a registered trademark of Bristol-Myers Squibb Co., New York, N.Y., for pharmaceutical preparations for the treatment and prevention of auto-immune diseases such as rheumatoid arthritis), also known as abatacept or CTLA-4Ig, were monitored in both commercial formulations and after exposure to pH 3 for 3 hours. Orencia® is a soluble fusion protein, consisting of the extracellular domain of human cytotoxic T-lymphocyte-associated antigen 4 (CTLA-4) fused to the modified Fc (hinge, CH2, and CH3 domains) portion of human immunoglobulin G1 (IgG1). Aggregates of CTLA-4Ig were pressure treated as a function of pH, pressure and additives as described below.

For sample preparation, aggregates were generated in 10 mM phosphate buffer at a pH of 3.0 at a protein concentration of 12 mg/ml. The samples were treated at these conditions until an aggregation extent of ~20% was achieved. The samples were then diluted to a concentration of 0.5 mg/ml in the appropriate solution conditions. The samples were placed into sealed syringes and pressure treated. Atmospheric controls were prepared under identical conditions and also stored in sealed syringes.

Pressurization was increased at a rate of 500 bar/minute until the desired pressure was achieved. During refolding, the temperature was maintained at 22 C (R.T.). The samples were held under pressure for approximately 16 hours and then were depressurized at a rate of 500 bar/five minutes. The samples were immediately prepared for SEC after depressurization.

Size Exclusion Analysis—High Pressure Liquid Chromatography (SEC) analysis of protein fractions was conducted on a Beckman Gold HPLC system (Beckman Coulter, Fullerton, Calif.) equipped with a TSK G3000 SW$_{XL}$ size exclusion column (Tosohaas). A filtered mobile phase of PBS (pH 7.2) at a rate of 1.0 ml/min was used, with an 10-25 ug protein sample injection from a Beckman 507e autosampler. Absorbance was monitored at 215 nm.

Aggregation of CTLA-4Ig at low pH was achieved by diluting commercial formulations to a protein concentration of 12 mg/ml and treated at pH 3 for 3 hours at 23° C. to induce aggregation. Two runs resulted in final aggregate concentrations of 15 and 21 percent respectively (Labeled Init % Agg.—FIG. 1). Aggregate analysis was quantified by SEC. High pressure treatment at pH 7 and higher resulted in ~95% refolding yields and aggregate levels lower than commercial CTLA-4Ig preparations (Orencia®).

Figure 1:
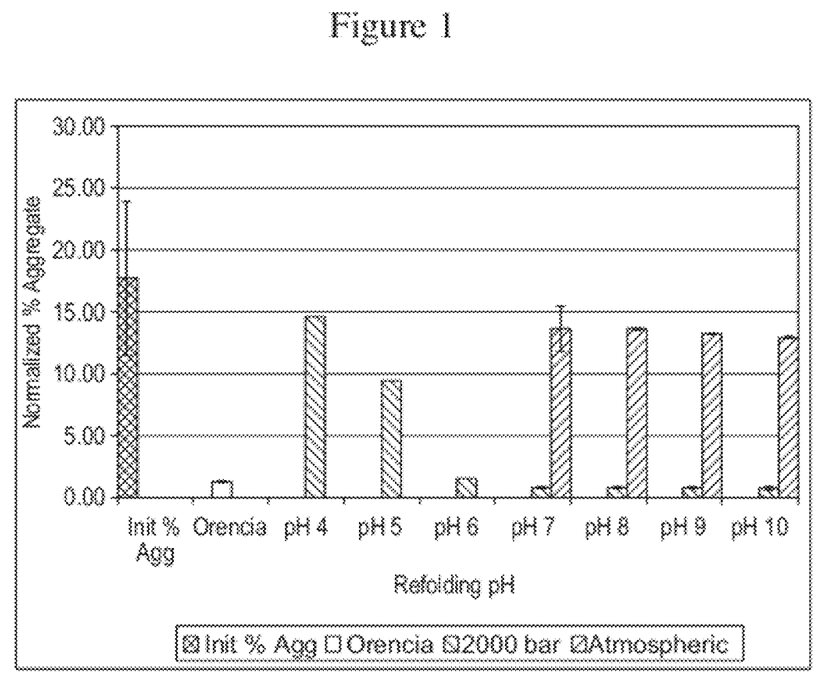
FIG. 1 depicts high pressure refolding of pH 3 induced aggregates of CTLA-4Ig (0.5 mg/ml) as a function of pH.

High pressure refolding of CTLA-4Ig as a function of pH is exemplified by aggregates (0.5 mg/ml) forming after exposure to pH 3, pressure treatment at 2000 bar for sixteen hours at 25° C. and compared to atmospheric controls (FIG. 1). Buffer concentrations were 10 mM to maintain a low ionic strength. Samples pressure treated in solutions of pH 7 or higher resulted in ~95% refolding yields, with a final aggregate concentration of 0.8%. The final aggregate concentration of 0.8% after pressure treatment is lower than what was present in the starting material prior to pH 3 induced aggregate (1.2%).

Atmospheric controls treated at identical temperature and solution conditions refolded to significantly lower levels relative to samples treated at high pressure. The basis for the decreased refolding at lower pHs is unknown. Error bars depict 95% confidence intervals. Throughout the entire analysis, total protein area was monitored to ensure that protein adsorption across the SEC column was minimal and the sizing method was quantifying aggregate levels accurately. Refolding at 5 mg/ml at pH 7.0 also resulted in refolding, with similar yields to the 0.5 mg/ml samples (data not shown).

Figure 2:
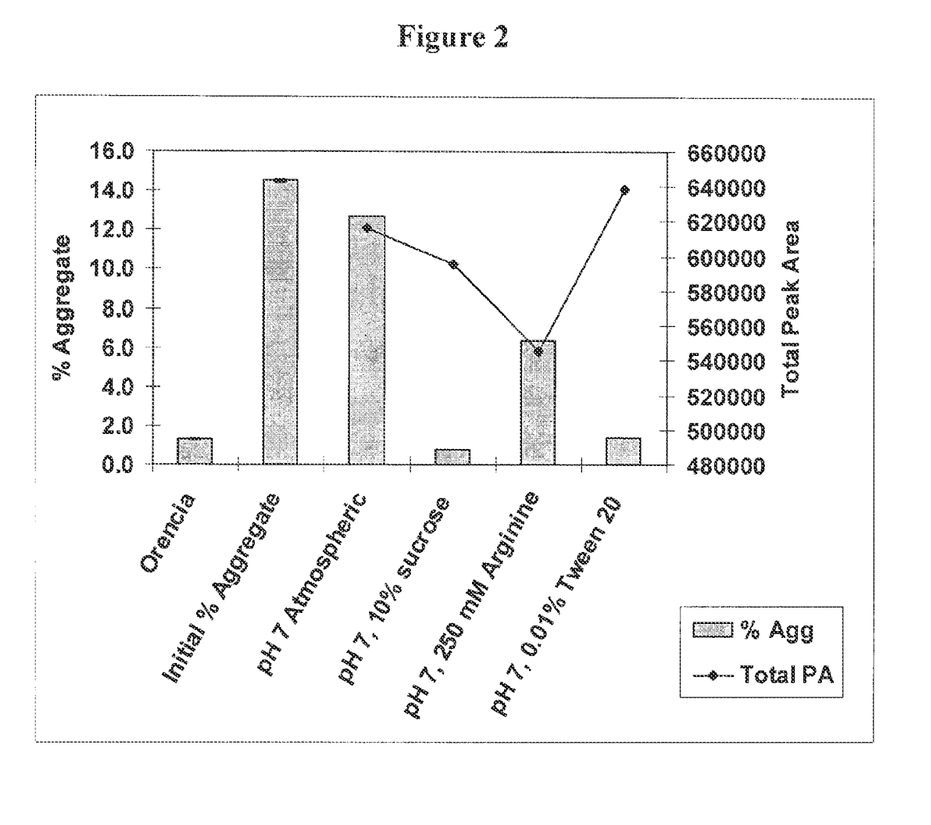
FIG. 2 depicts the effect of excipients on the refolding of CTLA-4Ig low pH induced aggregates.

Studies were conducted to examine high pressure refolding of CTLA-4Ig aggregates at pH 7.0 as a function of excipients; more specifically, to examine the effect of excipients (250 mM arginine, 10% (w/v) sucrose, and 0.01% (w/v) Tween 20) on the refolding yield of CTLA-4Ig acid-induced aggregates (0.5 mg/ml) at pH 7 (10 mM buffer) (FIG. 2). Excipients did not significantly increase the refolding yield over samples that were refolded in buffer alone (low ionic strength solution conditions) (FIG. 1). The presence of arginine decreased refolding yields; this data is consistent with an ionic-strength dependent effect. It was previously observed that high pressure treatment in the presence of 250 mM NaCl at pH 7 resulted in the aggregation of native CTLA-4Ig (data not shown).

Figure 3:
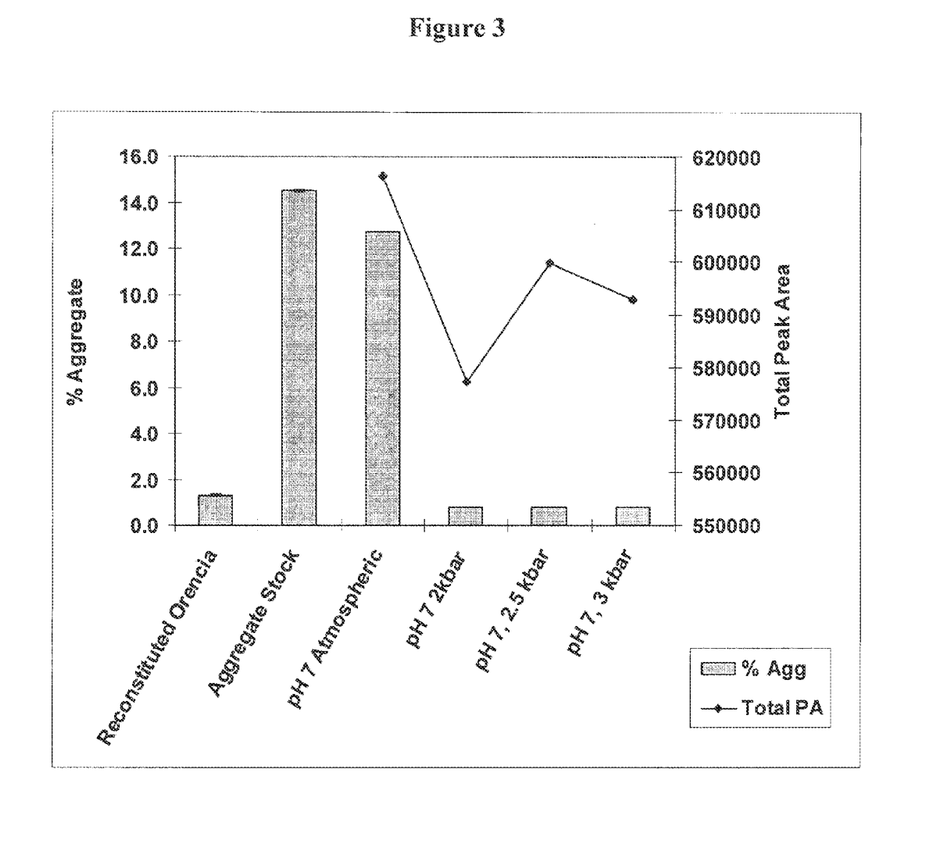
FIG. 3 depicts the effect of pressure on the refolding of CTLA-4Ig low pH induced aggregates.

To illustrate high pressure refolding of CTLA-4Ig aggregates at pH 7.0 as a function of pressure, aggregates of CTLA-4Ig (0.5 mg/ml) were treated at pH 7.0 (10 mM Buffer) as a function of pressure (0-3 kbar) at 25° C. for 16 hours. Pressures of 2000 bar were sufficient for the refolding of the aggregate with yields of ~95% relative to the initial aggregate concentration; increased pressures did not provide any increased yields (see FIG. 3).

Aggregation states of CTLA-4Ig were monitored in both commercial formulations and after exposure to pH 3 for 3 hours. Aggregates were pressure treated as a function of pH, pressure and additives. This illustrative study showed: high pressure refolded pH 3 induced aggregates of CTLA-4Ig (0.5 mg/ml), reducing aggregate levels from 18% to 0.8% (95% yield); high pressure refolding reduced the aggregate levels below those originally found in commercial formulations of CTLA-4Ig (Orencia®) being 0.8% vs. 1.3%, respectively; existing native protein is preserved during high pressure refolding in the appropriate solution conditions, however high pressure treatment in solutions of high ionic strength induced aggregation; refolding yields are not affected by moderate differences of initial aggregate concentrations (21% vs. 15%); refolding yields are pH dependent below pH 7; and, refolding pressures of 2000 to 3000 bar produce equivalent results Example 2

Use of High Pressure to Disaggregate and Refold Aggregates of the "Alliance mAb"

Aggregation states of a monoclonal antibody which was a gift of Alliance Laboratories were monitored after exposure to pH 3. The sequence and properties of this aggregate were unknown. Aggregates of the monoclonal antibody were pressure treated at a pH of 7.2 as a function of pressure and additives, as described below.

Aggregate samples were generated by dialysis into buffer at a pH of 3.0 at a protein concentration of 37 mg/ml. The samples were dialyzed in the buffer for six hours and then maintained at room temperature for six additional hours. The samples were then diluted to a concentration of either 0.3 or 5 mg/ml in the appropriate solution conditions. Buffer and ionic strength concentrations were 50 mM TES, pH 7.2, 150 mM NaCl. The samples were placed into sealed syringes and pressure treated. Atmospheric controls were prepared under identical conditions and also stored in sealed syringes.

Pressure was increased at a rate of 500 bar/minute until the desired pressure was achieved. During refolding, the temperature was maintained at 22 degrees C. (room temperature). The samples were held under pressure for approximately 16 hours and then were depressurized at a rate of 500 bar/five minutes. The samples were immediately prepared for SEC after depressurization.

Size Exclusion Analysis—High Pressure Liquid Chromatography (SEC) analysis of protein fractions was conducted on a Beckman Gold HPLC system (Beckman Coulter, Fullerton, Calif.) equipped with a TSK G3000 SW$_{XL}$ size exclusion column (Tosohaas). A filtered mobile phase of PBS (pH 7.2) at a rate of 1.0 ml/min was used from a Beckman 507e autosampler. Absorbance was monitored at 215 nm.

Aggregation of the Alliance mAb at low pH was induced by diluting 50 mg/ml formulations to a protein concentration of 33.5 mg/ml and exposure to pH 3 for 6 hours at 25° C. The final aggregate content was estimated to be 32% percent. Aggregate analysis was quantified by SEC.

Figure 4:
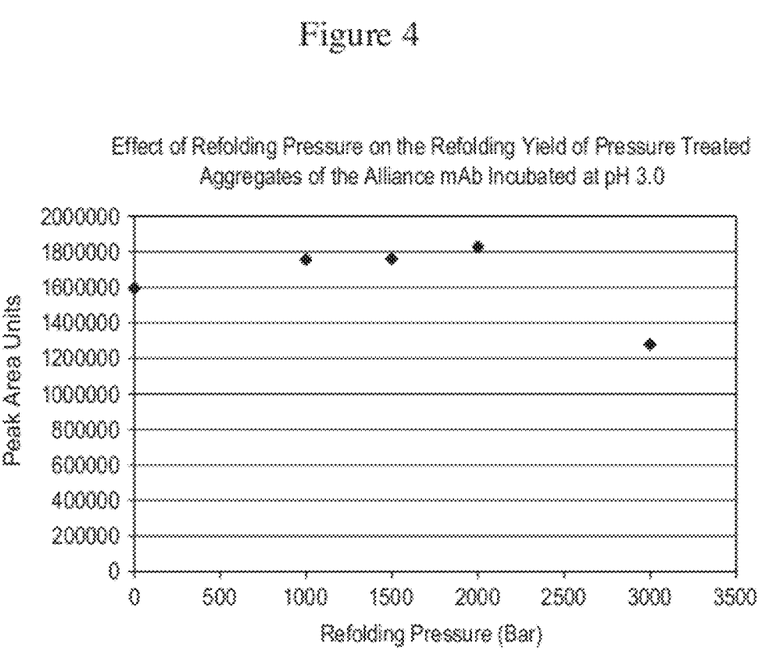
FIG. 4 depicts high pressure refolding of pH 3 induced aggregates of Alliance mAb as a function of pressure.

To illustrate high pressure refolding of Alliance mAb aggregates as a function of pressure, aggregates of the Alliance mAb (5 mg/ml) formed after exposure to pH 3 were pressure treated at 2000 bar for sixteen hours at 25° C. at a pH of 7.2. Pressures of 1 bar, 1000 bar, 1500 bar, 2000 bar and 3000 bar were tested. Of the samples tested, only aggregates pressure treated at 1000 to 2000 bar resulted in increased monomer content (FIG. 4). Aggregates pressure treated to 3000 bar resulted in increased aggregation, demonstrating the importance of the refolding window. Atmospheric controls treated at identical temperature and solution conditions also had lower monomer content. High pressure treatment at pressures of 1000-2000 bar resulted in the desired refolding.

Figure 5:
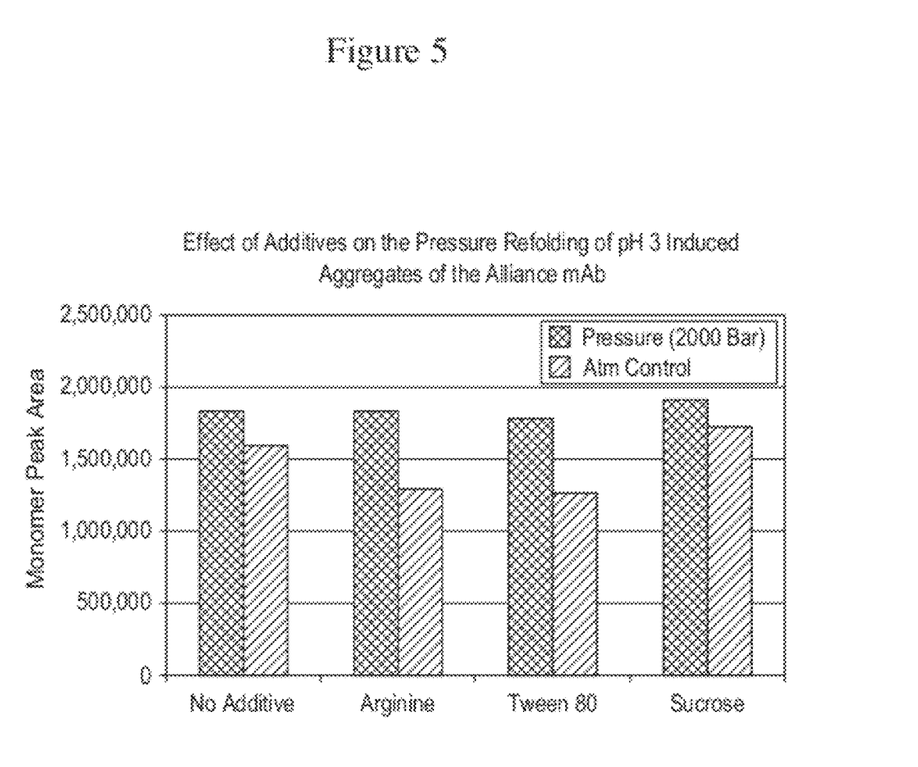
FIG. 5 depicts the effect of excipients on the pressure refolding of the Alliance mAb acid-induced aggregates.

Studies were conducted to examine high pressure refolding of Alliance mAb aggregates at pH 7.2 as a function of excipients. In order to examine the effect of excipients (250 mM arginine, 10% (w/v) sucrose, and 0.01% (w/v) Tween 80) on the refolding yield of Alliance mAb acid-induced aggregates (5 mg/ml) pH 7.2 (FIG. 5). Excipients did not significantly increase the refolding yield over samples that were refolded in buffer alone, i.e., at pH 7.2 without aggregates present (FIG. 5).

Figure 6:
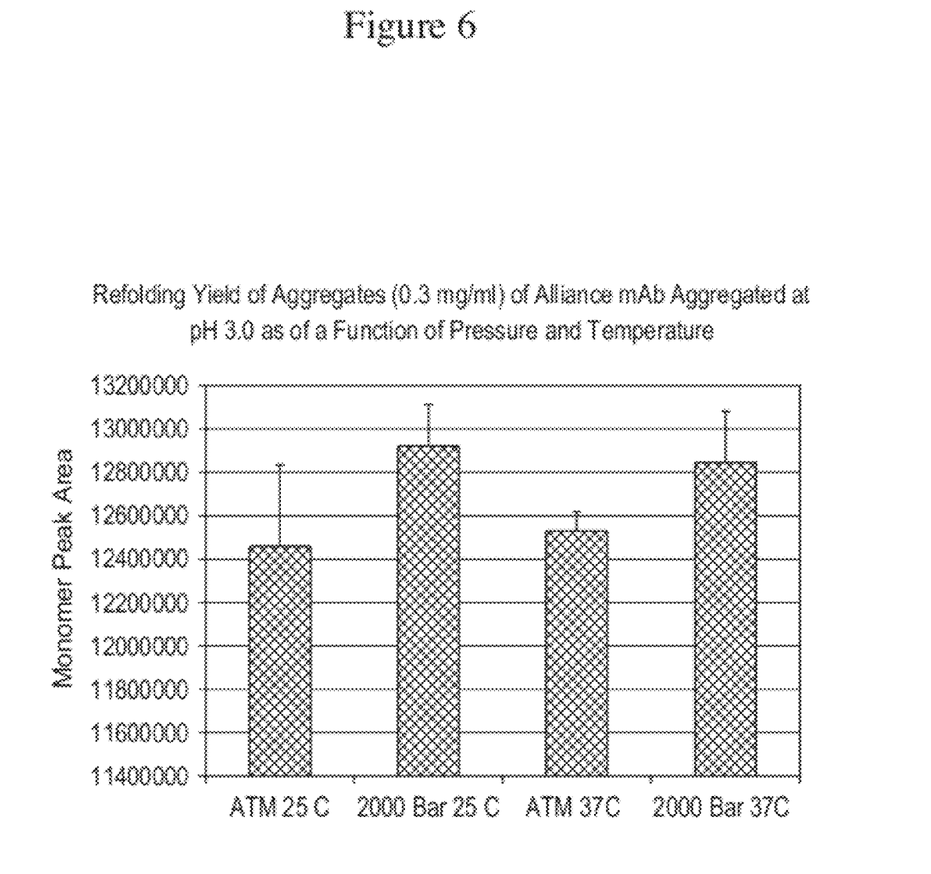
FIG. 6 depicts the effect of temperature on refolding of the Alliance mAb aggregated by exposure to pH 3.0.

To illustrate the high pressure refolding of the aggregates of the Alliance mAb, aggregates (0.3 mg/ml) were incubated at pH 7.2 as a function of temperature (25-37 degrees C.) for 16 hours. Pressures of 2000 bar at 25 degrees C. were sufficient for increasing the amount of monomer and increased temperature did not provide any increased yields. Increased temperature did not increase monomer peak area. (see FIG. 6).

Aggregation states of the Alliance mAb were monitored after exposure to pH 3.0. Aggregates of the mAb were pressure treated at a pH of 7.2 as a function of pressure and additives. This illustrative study showed: high pressure treatment of pH 3-induced aggregates at a pH of 7.2 resulted in increased monomer peak area as analyzed by SEC in comparison to atmospheric conditions, having values of 1.6 million and 1.8 million, respectively; addition of additives such as 250 mM arginine, 0.05% Tween 80, and 10% sucrose did not significantly effect the refolding yield of the Alliance mAb; elevated temperatures of 37° C. did not significantly increase the refolding yield of Alliance mAb aggregates at pressure treated to 2000 bar at pH 7.2 at 25° C.; and, pressures of 3000 bar induced aggregation of native mAb. Ongoing analytical ultracentrifugation (AUC) studies in order to quantify the refolding yields more accurately, as analysis of total peak area suggests that some protein adsorption may occur during SEC analysis.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method for refolding a sample of abatacept, comprising the steps of:
   (a) obtaining an abatacept sample comprising a solution of abatacept exposed to a pH of about 3 and containing from 15% to 21% acid-induced aggregates;
   (b) adjusting the of the solution to above 5;
   (c) exposing the abatacept to an increased hydrostatic pressure of about 1000 bar to about 3000 bar for a period of time; and
   (d) reducing the hydrostatic pressure to atmospheric pressure;
   wherein the sample of abatacept after exposure to increased hydrostatic pressure has less than about 1% abatacept aggregates than the abatacept sample prior to the increased pressure exposure.

2. The method of claim 1, wherein the content of monomeric and properly folded abatacept is measured by a method selected from a binding assay specific for abatacept, analytical ultracentrifugation, size exclusion chromatography, field flow fractionation, light scattering analysis, light obstruction analysis, fluorescence spectroscopy, gel electrophoresis, gas-phase electrophoretic mobility mass analysis (GEMMA), nuclear magnetic resonance spectroscopy, electron paramagnetic resonance spectroscopy, and reverse-phase chromatography.

3. The method of claim 1 wherein the concentration of abatacept in the abatacept sample is about 0.1 mg/mL to about 10 mg/mL.

4. The method of claim 1 wherein the ionic strength of the abatacept sample is less than about 100 mM.

5. The method of claim 1 wherein the amount of aggregated abatacept present in the abatacept sample alter pressure exposure is 0.8% or less.

* * * * *